United States Patent [19]

Wolfson

[11] 4,192,068
[45] Mar. 11, 1980

[54] ORTHODONTIC BAND AND SEATING TOOL THEREFOR

[75] Inventor: Joseph Wolfson, Trenton, N.J.

[73] Assignee: Charles Desenberg, Sarasota, Fla.

[21] Appl. No.: 756,058

[22] Filed: Jan. 3, 1977

[51] Int. Cl.² .............................................. A61C 7/00
[52] U.S. Cl. ........................................ 433/3; 433/23
[58] Field of Search ................ 32/14 A, 66, 51, 14 R, 32/63, 40 R; 81/3 E; 24/20 R

[56] References Cited

U.S. PATENT DOCUMENTS

| 159,173 | 1/1875 | Gaillard | 32/51 |
|---|---|---|---|
| 352,756 | 11/1886 | Husted | 32/54 |
| 1,204,114 | 11/1916 | Angle | 32/14 A |
| 1,215,442 | 2/1917 | Walker | 32/14 A |
| 1,229,024 | 6/1917 | Brandt | 32/40 R |
| 2,062,395 | 12/1936 | Brusse et al. | 32/14 A |
| 2,835,972 | 5/1958 | Sheldon | 32/66 |
| 3,034,215 | 5/1962 | Doster | 32/14 A |
| 3,797,116 | 3/1974 | Meeks, Jr. | 32/66 |
| 3,990,151 | 11/1976 | Kesling | 32/14 A |

OTHER PUBLICATIONS

"Bands Ad", Ormco Corporation catalog II, 5-1964, p. 6.

*Primary Examiner*—Louis G. Mancene
*Assistant Examiner*—John J. Wilson
*Attorney, Agent, or Firm*—Samuel Louis Sachs

[57] ABSTRACT

An orthodontic band and band seating tool therefor includes a seamless tubular band dimensioned to closely encircle a tooth. The band is provided with a plurality of integrally formed protrusions spaced thereabout with the integrally formed protrusions having an engagement surface adapted to cooperate with the band seating tool during the installation of the band about the tooth. The band seating tool provides an elongated handle and a seating element rotatably affixed to one end of the elongated handle, the seating element having a surface for cooperating with the engagement surface of the integrally formed protrusions.

14 Claims, 13 Drawing Figures

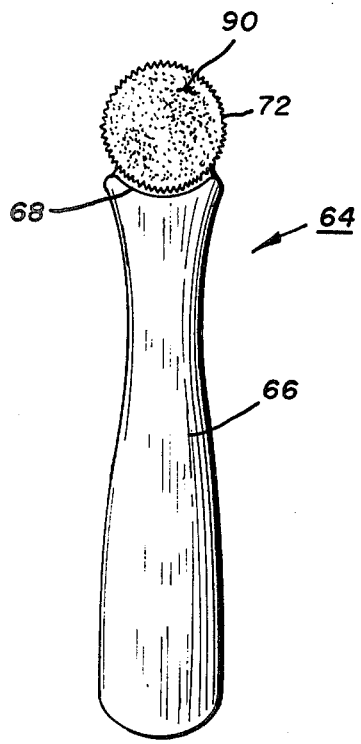
FIG.9
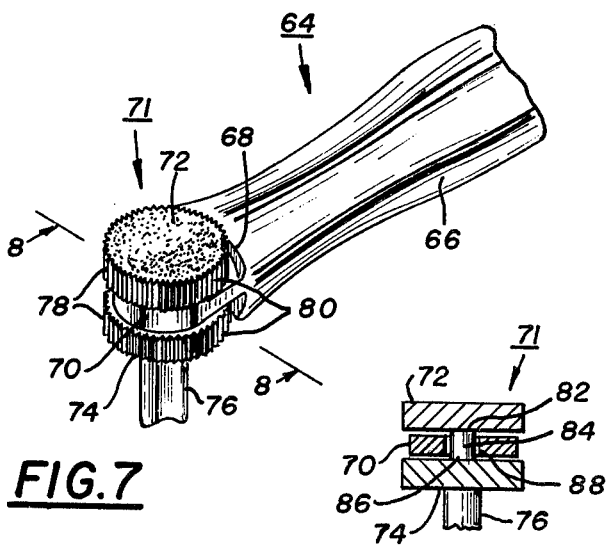
FIG.7
FIG.8
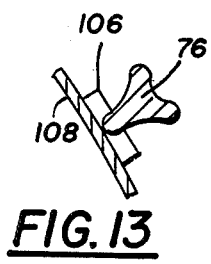
FIG.13
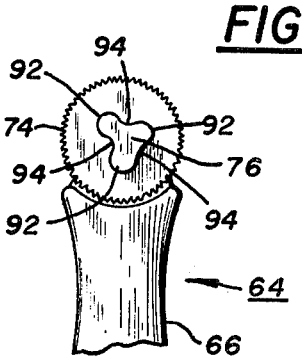
FIG.10
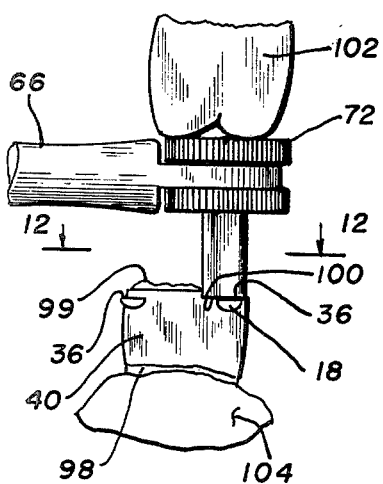
FIG.11
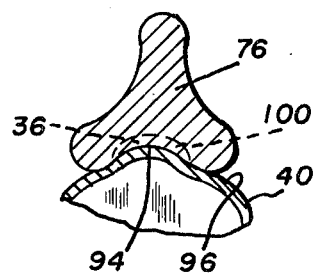
FIG.12

ORTHODONTIC BAND AND SEATING TOOL THEREFOR

BACKGROUND OF THE INVENTION

1. Field of the Invention

The present invention relates to dental appliances and the installation thereof, and more particularly, to an orthodontic band and seating tool therefor.

2. Description of the Prior Art

The use of dental appliances by orthodontic practitioners to effect the repositioning or stabilization of a tooth is well known. This method of dental correction frequently employs the use of orthodontic bands which are installed about a tooth by the orthodontist. Various hooks or brackets are attached to the orthodontic band, depending on the circumstances, and then the brackets or hooks are engaged by wires, rubber bands, or the like to accomplish the desired correction. A primary difficulty encountered with this method of dental correction is the installation of the orthodontic band about the tooth. Characteristically, orthodontic bands are manufactured of stainless steel in various sizes and shapes and are forced around the tooth causing the band to conform substantially thereto. The operation of forcing the orthodontic band around the tooth is a delicate task as excessive force may cause discomfort to the patient, splitting of the band, or damage to the tooth. Orthodontic bands are installed by several methods which include the tapping of the band in position by the orthodontist and by band seating tools which are placed in the patient's mouth, the patient exerting force upon the tool with the quidance of the orthodontist, thereby forcing the band into position around a tooth. Frequently, rectangular bars are welded to the band to provide a surface against which force can be exerted to install the band. Some common problems with utilizing these welded rectangular bars are the separation of the bar from the band during the seating operation and the tearing of misshaping of the band rendering it useless. Also, presently known band seating tools conform poorly to the welded rectangular bars inviting slippage or disengagement making installation of the orthodontic band difficult and possibly causing injury to the patient. Additionally, the shaped element provided by presently known band seating tools for engaging an orthodontic band during installation is fixed in position causing strategic problems when the orthodontic band must be installed in an inaccessible portion of the patient's mouth.

Typical of presently known orthodontic bands is the orthodontic appliance which is disclosed in U.S. Pat. No. 1,204,114 issued to E. H. Angle on Nov. 7, 1916. This ddvice includes a metallic circularly shaped band with a relatively small portion of the circumference being thicker than the remainder thereof. A hook for engagement by a wire or the like is fixedly secured to the band.

U.S. Pat. No. 1,215,442 issued to W. E. Walker on Feb. 13, 1917 discloses an orthodontic appliance which includes a band for placement around a tooth. In one embodiment the band is provided with a pair of recesses on opposed sides thereof and in another embodiment the band is provided with a plurality of protrusions having holes located therein. The grooves or apertures provided in the protrusions are used to capture and retain orthodontic wire or the like. Positioning of the band must be effected by the engagement of the edge of the band by a suitable dental instrument.

U.S. Pat. No. 1,062,395 issued to A. B. Brusse et al on Dec. 1, 1936 teaches a orthodontic appliance which includes a seamless tubular band that is open on both ends and is dimensioned to be placed around a tooth. Various types of flanges for affixment to the outer walls of the bands are illustrated and described. These flanges may be employed for anchoring wires and also for positioning the band about a tooth. The flanges are welded to the band as desired.

U.S. Pat. No. 3,797,116 issued to J. E. Meeks, Jr. on Mar. 19, 1974 reveals a dental band seater which includes an elongated handle portion that is flat adjacent to one end thereof. A pair of posts are fixedly secured to the flat portion of the handle. The free ends of the posts are intended to engage the free edges of a dental band to facilitate the installation of the band about a tooth. The device is designed to be used in a conventional manner with the opposed teeth of the patient employed to force the band into position.

The present invention overcomes the problems associated with the prior art by providing an orthodontic band having a plurality of integrally formed protrusions spaced strategically about the band to assist in the successful installation of the band about a tooth in conjunction with a band seating tool having a seating element for engaging the integrally formed protrusions, the seating element being rotatably positionable relative to the handle of the band seating tool.

SUMMARY OF THE INVENTION

Therefore, a primary object of the present invention is to provide an orthodontic band incorporating means to facilitate the uniform installation thereof.

A further object of the present invention is to provide an orthodontic band which does not necessitate the welding or soldering of extraneous material to the band to facilitate the installation thereof.

A still further object of the present invention is to provide an orthodontic band which may be seated about a tooth without excessive pressure.

Still another object of the present invention is to provide an orthodontic band which may be seated uniformly with minimal risk of the band tearing.

Another still further object of the present invention is to provide an orthodontic band which may be seated without excessive risk of fracturing a tooth.

Another object of the present invention is to provide an orthodontic band which will readily accept the affixment of any type of conventional bracket or attachment needed to aid in tooth movement.

Another further object of the present invention is to provide an orthodontic band which is suitable for use on centrals, laterals, cuspids, bicuspids, and molars.

Still another object of the present invention is to provide a band seating tool which may be utilized to seat most presently known orthodontic bands and which is ideally suited for installation of the orthodontic band of the present invention.

A still further object of the present invention is to provide a band seating tool which positively engages the orthodontic band of the present invention.

Another object of the present invention is to provide a band seating tool which may be employed easily in relatively inaccessible portions of a patient's mouth.

A further object of the present invention is to provide an orthodontic band and band seating tool therefor which are simple in design, inexpensive to manufacture, and durable.

These objects, as well as further objects and advantages, of the present invention will become readily apparent after reading the description of a non-limiting illustrative embodiment and the accompanying drawing.

An orthodontic band and a band seating tool for seating the orthodontic band about a tooth according to the principles of the present invention includes a continuous open-ended band dimensioned to closely encircle the tooth, the band having an inner surface for contacting the tooth and an outer surface, the outer surface being provided with a plurality of integrally formed protrusions spaced about the band, the integrally formed protrusions having an engagement surface adapted to cooperate with the band seating tool, the band seating tool including an elongated handle, a seating element having a surface for cooperating with the engagement surface of the orthodontic band, and means for rotatably affixing the seating element to one end of the handle, the longitudinal axis of the seating element being transverse to the longitudinal axis of the elongated handle.

BRIEF DESCRIPTION OF THE DRAWINGS

In order that the present invention may be more fully understood it will now be described, by way of example, with reference to the accompanying drawings in which:

FIG. 7 is a fragmentary pictorial representation of the band seating tool of the preferred embodiment according to the principles of the present invention;

FIG. 8 is a cross-sectional view of the rotatable element of the present invention taken substantially along the lines 8—8 of FIG. 7;

FIG. 9 is a top view of the band seating tool of FIG. 7;

FIG. 10 is a fragmentary bottom view of the band seating tool of FIG. 7;

FIG. 11 is a side view in elevation of the orthodontic band and band seating tool of the preferred embodiment in use;

FIG. 12 is a fragmentary cross-sectional view taken substantially along the lines 12—12 of FIG. 11;

FIG. 13 is a fragmentary cross-sectional view of the seating element of the preferred embodiment engaging a welded bar of a conventional orthodontic band.

DESCRIPTION OF THE PREFERRED EMBODIMENT

Figure 1:
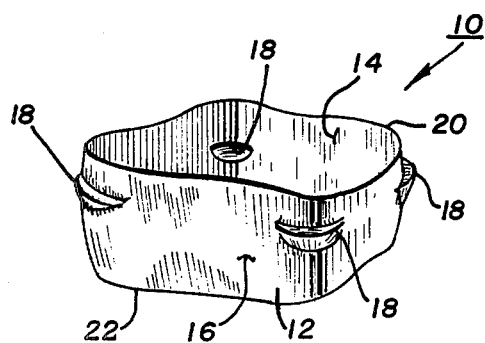
FIG. 1 is a pictorial representation of an orthodontic band for posterior teeth according to the principles of the present invention.

Referring now to the drawing, and more particularly to FIG. 1 thereof, there is illustrated therein an orthodontic band 10 for placement on a posterior tooth. The orthodontic band 10 includes a seamless tubular (continuous open-ended) band 12 fabricated of stainless steel or the like. The tubular band 12 provides a generally smooth inner surface 14 and a generally smooth outer surface 16. The tubular band 12 is dimensioned to closely encircle a tooth with the inner surface 14 thereof contacting the tooth when the band 12 is positioned thereon. The outer surface 16 of the seamless tubular band 12 is provided with a plurality of integrally formed protrusions 18 which are die formed and are spaced apart about the band as hereinafter described. When the orthodontic band 10 is seated around a tooth, a first edge 20 thereof falls adjacent to the incisal surface of the tooth and the second edge 22 of the orthodontic band 10 falls adjacent to the gingiva (gumline) of the patient. The first and second edges 20 and 22 of the band 12 are contoured in a customary fashion to conform to the gingiva and other needs of the patient.

Figure 2:
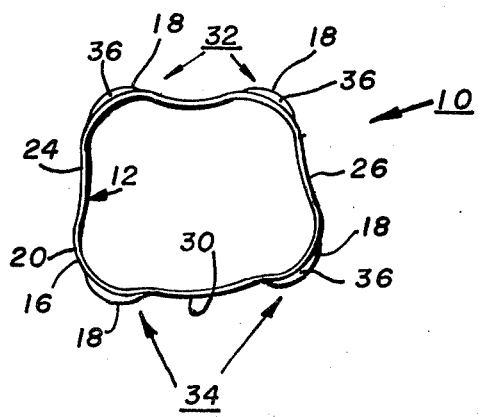
FIG. 2 is a top view of the orthodontic band of FIG. 1.

FIG. 2 is a top view of the orthodontic band 10 and illustrates the preferred positioning of the integrally formed protrusions 18 upon the outer surface 16 of the seamless tubular band 12. The orthodontic band 10 provides a pair of opposed proximal or side surfaces 24 and 26, a lingual surface 28, and a facial surface 30. For convenience, the integrally formed protrusions 18 will be referred to as a first pair of protrusions 32 and a second pair of protrusions 34. The first pair 32 of integrally formed protrusions 18 are located on the lingual surface 28 of the orthodontic band 10 and each partially extend into the adjacent proximal surfaces 24 or 26. The second pair 34 of integrally formed protrusions 18 are located on the facial surface 30 of the orthodontic band 10 and partially extend into the adjacent proximal surface 24 or 26 thereof. The location of the integrally formed protrusions 18 as described above provide for uniform seating and even distribution of force when the orthodontic band 10 is installed on a tooth. Each of the integrally formed protrusions 18 provide an engagement surface 36 which is substantially flat.

Figure 3:
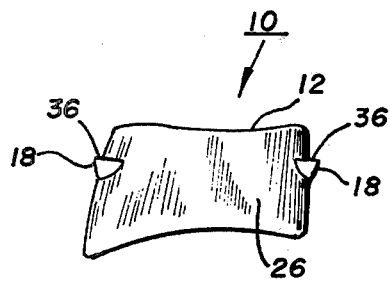
FIG. 3 is a side view in elevation of the orthodontic band of FIG. 1.

FIG. 3 is a side view of the orthodontic band 10 and clearly illustrates the extension of two of the integrally formed protrusions 18 into the mesial surface 26. When the orthodontic band 10 is placed about a tooth, the engagement surfaces 36 of the integrally formed protrusions 18 fall adjacent to the incisal surface of the tooth.

Figure 4:
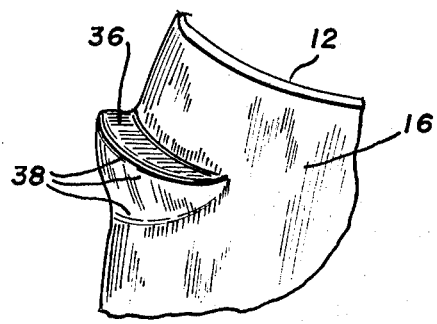
FIG. 4 is an enlarged fragmentary pictorial side view of one of the integrally formed protrusions of the preferred embodiment.

FIG. 4 is an enlarged pictorial view of one of the integrally formed protrusions 18 of the preferred embodiment. Each of the integrally formed protrusions 18 are preferably substantially quadraspherical in shape. The quadraspherical shape is that of a bifurcated hemisphere with one flat surface disposed adjacent to the band 12 and the other flat surface serving as the engagement surface 36. The outermost surfaces 38 of each of the integrally formed protrusions 18 taper downwardly toward the outer surface 16 of the seamless tubular band 12. The engagement surface 36 lies in a plane substantially perpendicular to the outer surface 16 of the band 12. As a result, no sharp surfaces are presented which may cause irritation to the buccal, lingual, or labial surfaces of a patient's mouth. The engagement surface 36 is adapted to cooperate with a band seating tool or the like. The integrally formed protrusions 18 are formed at the time the orthodontic band 10 is manufactured. This is preferably accomplished by the use of suitable dies or the like presently known in the manufacturing arts which push the integrally formed protrusions 18 outwardly from tubular stainless steel stock and cut the stock into a plurality of sections thereby forming a plurality of structures as described. Although four integrally formed protrusions spaced as described above are considered to be optimal, additional integrally formed protrusions 18 may be added or subtracted as desired.

Figure 5:
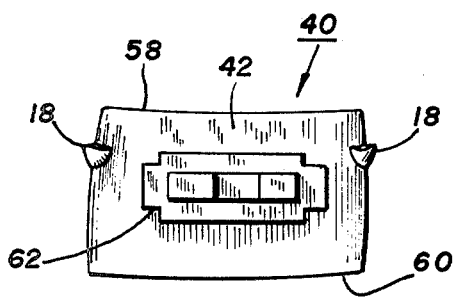
FIG. 5 is a front view in elevation of an orthodontic band for anterior teeth according to the principles of the present invention.
Figure 6:
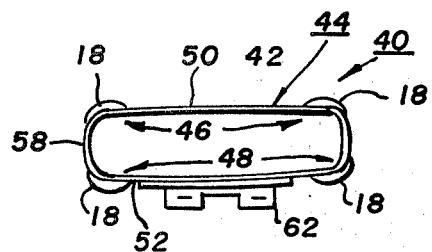
FIG. 6 is a top view of the band of FIG. 5.

FIGS. 5 and 6 illustrate, respectively, a front and top view of an orthodontic band 40 incorporating therein the principles of the present invention for use of an anterior tooth. The orthodontic band 40 includes a seamless tubular (continuous open-ended) band 42 preferably fabricated of stainless steel and is similar in construction to the seamless tubular band 12 of the orthodontic band 10 except for dimensioning. The outer surface 44 of the seamless tubular band 42 is provided with a plurality of integrally formed protrusions 18 configured in a first pair 46 and a second pair 48. The first pair 46 of integrally formed protrusions 18 are located on the lingual surface 50 of the orthodontic band 40, and the second pair 48 of integrally formed protrusions 18 are located on the facial surface 52 thereof. Each of the integrally formed protrusions 18 extend into the adjacent proximal surface 54 or 56. When the orthodontic band 40 is installed on a tooth, the first edge 58 thereof falls adjacent to the incisal surface of the tooth and the second edge 60 of the orthodontic band 40 falls adjacent to the gingiva of the patient. The ideal positioning of the plurality of integrally formed protrusions is such that a hypothetical division of the seamless tubular band 42 into thirds would find the integrally formed protrusions 18 residing in the third closest to the first edge 58, as illustrated. The size an placement of the integrally formed protrusions 18 are such that a bracket 62 or other similar attachment may be affixed to the tubular band 42 without interference. The bracket 62 or other attachment is employed to engage a wire, rubber band, or the like to effect orthodontic corrections and would be welded to the seamless tubular band 42 in a conventional manner.

The orthodontic bands 10 and 40 may be installed about the tooth of a patient by presently known mechanical or manual tapping methods as well as with the use of a "bite stick" tool or the like. However, the orthodontic bands 10 and 40 are ideally suited for installation by the band seating tool of the present invention.

FIG. 7 illustrates a perspective view of a band seating tool 64 incorporating therein the principles of the present invention. The band seating tool 64 includes an elongated handle 66 having an end 68. The elongated handle 66 is contoured as illustrated to facilitate the grasping thereof by the user. The elongated handle 66 provides an extensive flange 70 adjacent to the end 68 thereof. A rotatable element 71 including a pair of disks 72 and 74 is rotatably disposed, respectively, above and below the flange 70 as further illustrated in FIG. 8. A seating element 76 is fixedly secured to the disk 74 so that the longitudinal axis of the elongated handle 66 is preferably substantially perpendicular to the longitudinal axis of the seating element 76. The edges 78 of the pair of disks 72 and 74 are provided with striations 80 to facilitate the gripping thereof by the user. The elongated handle 66 of the disks 72 and 74 are preferably constructed of a hard durable plastic such as Cycolac or the like.

FIG. 8 is a cross-sectional view of the band seating tool 64 illustrating the manner in which the pair of disks 72 and 74 rotatably cooperate with the extensive flange 70. The disk 72 is fixedly secured to one end 82 of a shaft 84. The other end 86 of the shaft 84 is fixedly secured to the disk 74. The shaft 84 is journaled within an aperture 88 located in the extensive flange 70. Either of the disks 72 or 74 may be turned by the thumb of the user to position the seating element 76 correctly for installation of an orthodontic band.

In use the seating element 76 is positioned by the user by rotation of the rotatable element 71 and is placed in contact with the orthodontic band. The patient then exerts force upon the disk 72 with his teeth opposite the tooth the band is to be seated around. The pressure the patient exerts on the upper disk 72 causes the flange 70 to be tightly sandwiched between the pair of disks 72 and 74 thereby precluding any rotation of the rotatable element 71 during use.

FIG. 9 is a top view of the band seating tool 64 and illustrates the manner in which the elongated handle 66 is contoured to facilitate the grasping thereof. The uppermost surface 90 is provided with a friction inducing surface such as the pebbling illustrated to preclude the teeth of the patient from slipping thereoff during the band seating process.

FIG. 10 is a fragmentary bottom view of the seating element 76 fixedly secured to the disk 74. The seating element 76 has a substantially triangular cross section with the vertexes 92 being rounded and the legs 94 being inwardly arcuate. The radius of curvature of each of the legs 94 conform substantially to the radius of curvature of the outer surface 96 of the orthodontic bands 10 and 40 adjacent to the integrally formed protrusions 18 as further illustrated in FIG. 12.

FIG. 11 illustrates the orthodontic band 40 being installed on a first tooth 98. The band 40 is oriented so that the engagement surfaces 36 provided by the integrally formed protrusions 18 are proximate to the incisal surface 99 of the first tooth 98. The lowermost surface 100 of the seating element 76 engages the engagement surface 36 provided by the integrally formed protrusion 18. A second tooth 102 of the patient places pressure on the disk 72 thereby forcing the orthodontic band 40 toward the gingiva 104 of the patient. The band seating tool 64 is moved in succession from one integrally formed protrusion 18 to another to apply pressure for uniformly forcing the band 40 until it assumes the proper position about the tooth 98. Since the seating element 76 of the band seating tool 64 is rotatable relative to the elongated handle 66 thereof, the band seating tool 64 can be employed in almost any location in the mouth of the patient, thereby precluding the need to stretch or distort the mouth of the patient while the band seater is being utilized to effect the installation of the orthodontic band 40.

FIG. 12 is an enlarged cross-sectional view showing the manner in which the lowermost surface 100 of the seating element 76 engages the engagement surface 36 provided by the integrally formed protrusions 18 of the orthodontic bands 10 and 40. The radius of curvature of the legs 94 of the shaft 84 conforms substantially to the outer surface 96 of the orthodontic bands 10 and 40 adjacent to the integrally formed protrusions 18 thereof. As a result, the seating element 76 firmly engages orthodontic band 40 and is prevented from slipping thereoff which may cause possible injury to the patient.

FIG. 13 illustrates the seating element 76 of the band seating tool 64 engaging a rectangular bar 106 welded on a conventional band 108. Although the band seating tool is ideally adapted for use with the orthodontic bands 10 and 40 of the present invention, it may also be effectively employed to seat presently known orthodontic bands as shown. The band seating tool 64 of the present invention is particularly helpful in seating presently known bands because free rotation of the rotatable element 71 and therefore the seating element 76 is permitted. The seating element 76 of the band seating tool 64 is preferably constructed of hardened stainless steel and may be configured in other shapes for use in conjunction with various types of presently known orthodontic appliances.

Therefore, a primary advantage of the present invention is to provide an orthodontic band incorporating means to facilitate the uniform installation thereof.

A further advantage of the present invention is to provide an orthodontic band which does not necessitate the welding or soldering of extraneous material to the band to facilitate the installation thereof.

A still further advantage of the present invention is to provide an orthodontic band which may be seated about a tooth without excessive pressure.

Still another advantage of the present invention is to provide an orthodontic band which may be seated uniformly with minimal risk of the band tearing.

Another still further advantage of the present invention is to provide an orthodontic band which may be seated without excessive risk of fracturing a tooth.

Another advantage of the present invention is to provide an orthodontic band which will readily accept the affixment of any type of conventional bracket or attachment needed to aid in tooth movement.

A further advantage of the present invention is to provide an orthodontic band which is suitable for use on centrals, laterals, cuspids, bicuspids, and molars.

Still another advantage of the present invention is to provide a band seating tool which may be utilized to seat most presently known orthodontic bands and which is ideally suited for installation of the orthodontic band of the present invention.

A still further advantage of the present invention is to provide a band seating tool which positively engages the orthodontic band of the present invention.

Another advantage of the present invention is to provide a band seating tool which may be employed easily in relatively inaccessible portions of a patient's mouth.

A further advantage of the present invention is to provide an orthodontic band and band seating tool therefor which are simple is design, inexpensive to manufacture, and durable.

it will be understood that various changes in the details, materials, arrangements of parts and operation conditions which have been herein described and illustrated in order to explain the nature of the invention may be made by those skilled in the art within the principles and scope of the invention.

Having thus set forth the nature of the invention, what is claimed is:

1. An orthodontic band for affixment about a tooth comprising a continuous open-ended band dimensioned to closely encircle said tooth, said open ends of said band terminating at an incisal edge and a gingival edge, said band having an inner surface for contacting said tooth and an outer surface, said inner and outer surfaces being interposed between said incisal and said gingival edges, said outer surface being provided with a plurality of integrally formed protrusions spaced about said band, said integrally formed protrusions having a rigid substantially planar engagement surface adapted to cooperate with a band seating tool, said integrally formed protrusions each being disposed a preselected distance from said incisal and gingival edges, said rigid substantially planar engagement surface being solid and continuous and tapering from said outer surface.

2. An orthodontic band according to claim 1, wherein said engagement surface of each of said plurality of integrally formed protrusions is oriented proximate to said incisal edge of said band which is disposed adjacent to the incisal surface of said tooth when said band is positioned about said tooth.

3. An orthodontic band according to claim 1, wherein each of said plurality of integrally formed protrusions are substantially quadraspherical in shape, the outermost surfaces of each of said integrally formed protrusions tapering toward said outer surface of said band, said engagement surface of each of said plurality of integrally formed protrusions being substantially planar for facilitating the contact of said band seating tool therewith.

4. An orthodontic band according to claim 1, wherein said plurality of integrally formed protrusions comprise a first pair and a second pair.

5. An orthodontic band according to claim 4, wherein said first pair of said integrally formed protrusions are disposed on a portion of said band substantially adjacent to the facial surface of said tooth when said band is positioned thereon, said first pair of integrally formed protrusions being spaced apart and partially extending into a portion of said band adjacent to the proximal surfaces of said tooth, said second pair of said integrally formed protrusions being disposed on a portion of said band substantially adjacent to the lingual surface of said tooth, said second pair of integrally formed protrusions being spaced apart and partially extending into a portion of said band adjacent to said proximal surfaces of said tooth.

6. An orthodontic band according to claim 1, wherein each of said plurality of integrally formed protrusions are disposed on a portion of said band adjacent to said incisal surface of said tooth when said band is positioned about said tooth.

7. An orthodontic band according to claim 6, wherein each of said plurality of integrally formed protrusions are disposed on the third thereof adjacent to the incisal surface of said tooth when said band is positioned about said tooth.

8. An orthodontic band for affixment about a tooth comprising a continuous open-ended band dimensioned to closely encircle said tooth, said open ends of said band terminating at an incisal edge and a gingival edge, said band having an inner surface for contacting said tooth and an outer surface, said inner and outer surfaces being interposed between said incisal and said gingival edges, said outer surface being provided with a plurality of integrally formed protrusions spaced about said band, said integrally formed protrusions having a rigid substantially planar engagement surface adapted to cooperate with a band seating tool, said integrally formed protrusions each being disposed a preselected distance from said incisal and gingival edges, said engagement surface of each of said plurality of integrally formed protrusions being oriented proximate to said incisal edge of said band which is disposed adjacent to the incisal surface of said tooth when said band is positioned about said tooth, each of said plurality of integrally formed protrusions being substantially quadraspherical in shape, the outermost surfaces of each of said integrally formed protrusions tapering toward said outer surface of said band, said engagement surface of each of said plurality of integrally formed protrusions being substantially planar for facilitating the contact of said band seating tool therewith, said plurality of integrally formed protrusions including a first pair and a second pair, said first pair of integrally formed protrusions being disposed on a portion of said band substantially adjacent to the facial surface of said tooth when said band is positioned thereon, said first pair of integrally formed protrusions being spaced apart and partially extending into a portion of said band adjacent to the proximal surfaces of said tooth, said second pair of integrally formed protrusions being disposed on a portion of said band substantially adjacent to the lingual surface of said tooth, said second pair of integrally formed protrusions being spaced apart and partially extending into a portion of said band adjacent to the proximal surfaces of said tooth, each of said plurality of integrally formed protrusions being disposed on the third thereof adjacent to said incisal surface of said tooth when said band is positioned about said tooth.

9. A band seating tool for seating orthodontic bands about a tooth comprising:
an elongated handle;
a seating element having a surface for cooperating with a portion of said orthodondic band; and
means for rotatably affixing said seating element to one end of said handle, the longitudinal axis of said seating element being fixed at a location transverse to the longitudinal axis of said elongated handle, said seating element being rotatable about the longitudinal axis thereof, said rotatable affixing means comprising an extensive flange provided by said one end of said elongated handle, said flange having an aperture therethrough, a rotatable element including a pair of spaced apart disks, said seating element being fixedly secured to one of said disks, and a shaft having a first and a second end, said first end fixedly secured to one of said disks, said second end fixedly secured to the other of said disks, said shaft being journaled in said aperture, said pair of disks thereby sandwiching said flange.

10. A band seating tool according to claim 9, wherein the edges of said disks are provided with striations.

11. A band seating tool according to claim 9, wherein said other disk has the external surface thereof facing away from said flange provided with a friction inducing surface.

12. A band seating tool according to claim 9, wherein said seating element has a substantially triangular cross section with the vertexes of said triangle being rounded and the legs of said triangle being inwardly arcuate.

13. A band seating tool for seating orthodontic bands about a tooth comprising:
an elongated handle;
a seating element having a surface for cooperating with a portion of said orthodontic band, said seating element having a substantially triangular cross section with the vertexes of said triangle being rounded and the legs of said triangle being inwardly arcuate; and
means for rotatably affixing said seating element to one end of said handle, the longitudinal axis of said seating element being transverse to the longitudinal axis of said elongated handle, said rotatable affixing means including an extensive flange provided by said one end of said elongated handle, said flange having an aperture therethrough, a rotatable element including a pair of spaced apart disks, said seating element being fixedly secured to one of said disks, and a shaft having a first and a second end, said first end fixedly secured to said one of said disks, said second end fixedly secured to said other of said disks, said shaft being journaled in said aperture, said pair of disks thereby sandwiching said flange, the edges of said disks being provided with striations, said other disk having the external surface thereof facing away from said flange provided with a friction inducing surface.

14. An orthodontic band and a band seating tool for seating said orthodontic band about a tooth comprising a continuous open-ended band dimensioned to closely encircle said tooth, said band having an inner surface for contacting said tooth and an outer surface, said outer surface being provied with a plurality of integrally formed protrusions spaced about said band, said integrally formed protrusions having an engagement surface for cooperating with said band seating tool, said engagement surface of each of said plurality of integrally formed protrusions being oriented proximate to the edge of said band adjacent to the incisal surface of said tooth when said band is positioned about said tooth, each of said plurality of integrally formed protrusions being substantially quadraspherical in shape, the outermost surfaces of each of said integrally formed protrusions tapering toward said outer surface of said band, a portion of said engagement surface of each of said plurality of integrally formed protrusions being substantially flat for facilitating the contact of said band seating tool therewith, said plurality of integrally formed protrusions including a first pair and a second pair, said first pair of integrally formed protrusions being disposed on a portion of said band substantially adjacent to the facial surface of said tooth when said band is positioned thereon, said first pair of integrally formed protrusions being spaced apart and partially extending into a portion of said band adjacent to the proximal surfaces of said tooth, said second pair of integrally formed protrusions being disposed on a portion of said band substantially adjacent to the lingual surface of said tooth, said second pair of integrally formed protrusions being spaced apart and partially extending into a portion of said band adjacent to said proximal surfaces of said tooth, each of said plurality of integrally formed protrusions being disposed on the third thereof adjacent to said incisal surface of said tooth when said band is positioned about said tooth, said tool having an elongated handle, a seating element providing a surface for cooperating with said engagement surface of said orthodontic band, said seating element having a substantially triangular cross section with the vertexes of said triangle being rounded and the legs of said triangle being inwardly arcuate, the radius of curvature of each of said arcuate legs substantially conforming to the radius of curvature of the portions of said band adjacent to each of said plurality of integrally formed protrusions, and means for rotatably affixing said seating element to one end of said handle, the longitudinal axis of said seating element being transverse to the longitudinal axis of said elongated handle, said rotatable affixing means including an extensive flange provided by said one of said elongated handle, said flange having an aperture therethrough, a rotatable element including a pair of spaced apart disks, said seating element being fixedly secured to one of said disks, and a shaft having a first end and a second end, said first end fixedly secured to one of said disks, said second end fixedly secured to said other of said disks, said shaft being journaled in said aperture, said pair of disks thereby sandwiching said flange, the edges of said disks being provided with striations, said other disk having the external surface thereof facing away from said flange provided with a friction inducing surface.

* * * * *